US009955992B2

(12) United States Patent
Pravong et al.

(10) Patent No.: US 9,955,992 B2
(45) Date of Patent: May 1, 2018

(54) METHOD AND APPARATUS FOR TISSUE MORCELLATION

(71) Applicant: Applied Medical Resources Corporation, Rancho Santa Margarita, CA (US)

(72) Inventors: Boun Pravong, Rancho Santa Margarita, CA (US); Kennii Pravongviengkham, Rancho Santa Margarita, CA (US); Matthew M. Becerra, Rancho Santa Margarita, CA (US); Matthew A Wixey, San Jose, CA (US); Haruyasu Yawata, Huntington Beach, CA (US); Gary M. Johnson, Rancho Santa Margarita, CA (US); Zoran Falkenstein, Rancho Santa Margarita, CA (US); John R. Brustad, Rancho Santa Margarita, CA (US); Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1041 days.

(21) Appl. No.: 13/659,462

(22) Filed: Oct. 24, 2012

(65) Prior Publication Data

US 2013/0046140 A1    Feb. 21, 2013

Related U.S. Application Data

(63) Continuation of application No. 12/102,719, filed on Apr. 14, 2008, now Pat. No. 8,308,746.

(Continued)

(51) Int. Cl.
A61B 17/32 (2006.01)
A61B 17/3205 (2006.01)
(Continued)

(52) U.S. Cl.
CPC .. *A61B 17/32002* (2013.01); *A61B 17/32053* (2013.01); *A61B 17/29* (2013.01);
(Continued)

(58) Field of Classification Search
CPC ........ A61B 17/32002; A61B 17/32053; A61B 17/29; A61B 2017/00902;
(Continued)

(56) References Cited

U.S. PATENT DOCUMENTS 4,160,450 A    7/1979 Doherty
4,483,562 A *  11/1984 Schoolman ............ A61B 17/29
                                                            294/104
(Continued)

OTHER PUBLICATIONS

The International Searching Authority (US), The International Search Report and the Written Opinion of the International Search Authority for International Application No. PCT/US08/60243 dated Sep. 4, 2008.

(Continued)

*Primary Examiner* — Elizabeth Houston
*Assistant Examiner* — Tin Nguyen
(74) *Attorney, Agent, or Firm* — Rimas T. Lukas

(57) ABSTRACT

The invention relates to a tissue morcellator for minimally invasive surgery. The morcellator has a metallic cutting ring mounted on a visually transparent hollow cylinder, which in combination with a visually transparent outer morcellator tube enables a surgeon to visualize the inside of the morcellator shaft for detection of loose tissue fragments in the device. A tenaculum used with the morcellation device has a spacer for preventing contact with the blade. The cutting (Continued)

tube can oscillate, rather than rotate, along the longitudinal axis of the cutting tube. The morcellator utilizes an extendable tissue guide on the outer tube of the morcellator shaft for preventing the tissue from rotating along the longitudinal axis of the morcellator tube. This allows the tissue to be continuously rotated into the morcellator device for continuous peel. The tissue guide can also be fully retracted to allow for coring of the bulk tissue.

15 Claims, 8 Drawing Sheets

Related U.S. Application Data

(60) Provisional application No. 60/911,444, filed on Apr. 12, 2007.

(51) Int. Cl.
*A61B 17/29* (2006.01)
*A61B 17/00* (2006.01)
*A61B 17/3207* (2006.01)
*A61B 90/00* (2016.01)

(52) U.S. Cl.
CPC ... *A61B 90/361* (2016.02); *A61B 2017/00902* (2013.01); *A61B 2017/2948* (2013.01); *A61B 2017/320024* (2013.01); *A61B 2017/320775* (2013.01)

(58) Field of Classification Search
CPC ....... A61B 2017/320024; A61B 2017/320775; A61B 2017/2948; A61B 19/5212
USPC ........................................... 606/169; 600/104
See application file for complete search history.

(56) References Cited

U.S. PATENT DOCUMENTS

| | | | |
|---|---|---|---|
| 4,570,624 A | | 2/1986 | Wu |
| 4,601,290 A | | 7/1986 | Effron et al. |
| 4,785,826 A | | 11/1988 | Ward |
| 5,336,176 A | | 8/1994 | Yoon |
| 5,346,497 A | | 9/1994 | Simon et al. |
| 5,423,330 A | | 6/1995 | Lee |
| 5,520,634 A | | 5/1996 | Fox et al. |
| 5,569,290 A | * | 10/1996 | McAfee ................ 606/185 |
| 6,039,748 A | * | 3/2000 | Savage et al. ............ 606/180 |
| 6,045,566 A | | 4/2000 | Pagedas |
| 6,139,509 A | | 10/2000 | Yuan et al. |
| 6,436,107 B1 | * | 8/2002 | Wang et al. ............. 606/139 |
| 6,572,632 B2 | | 6/2003 | Zisterer et al. |
| 6,610,072 B1 | | 8/2003 | Christy et al. |
| 2003/0050639 A1 | | 3/2003 | Yachia et al. |
| 2005/0261676 A1 | * | 11/2005 | Hall et al. ................ 606/48 |
| 2006/0189920 A1 | * | 8/2006 | Seeh ............... A61B 17/32002 604/22 |
| 2007/0219549 A1 | | 9/2007 | Marshall et al. |
| 2008/0039880 A1 | | 2/2008 | Nohilly et al. |
| 2008/0039883 A1 | * | 2/2008 | Nohilly ........... A61B 17/32002 606/180 |

OTHER PUBLICATIONS

The International Bureau of WIPO, International Preliminary Report on Patentability for International Application No. PCT/US08/060243 dated Oct. 13, 2009.

* cited by examiner

METHOD AND APPARATUS FOR TISSUE MORCELLATION

CROSS-REFERENCE TO RELATED APPLICATIONS

This application is a continuation of U.S. patent application Ser. No. 12/102,719 now U.S. Pat. No. 8,308,746 entitled "Method and apparatus for tissue morcellation" filed on Apr. 14, 2008 which claims benefit and priority to U.S. Provisional Patent Application No. 60/911,444, filed on Apr. 12, 2007, both of which are hereby incorporated by reference in their entirety as if set forth in full herein.

FIELD

The present invention relates generally to the field of minimally invasive surgery, and in particular to a method and apparatus for the morcellation and extraction of biological, human tissue through a hollow cylindrical cutting tube that is rotated along its longitudinal axis, preferably configured as a hand-held laparoscopic device. The instrument allows visual observation of the tissue extraction through the cutting tube. The instrument also incorporates a tissue guide or manipulator that can be extended beyond the distal position of the cutting blade of the tool, preventing both the coring of the tool into the tissue, as well as rotation of the tissue along the longitudinal axis of the morcellation tool.

BACKGROUND

Several laparoscopic procedures require the bulk removal of body tissue or organs through a limited surgical opening. As such, the tissue needs to be morcellated within the body cavity into smaller pieces of tissue from where they can be removed with laparoscopic graspers or tenaculums through minimally invasive access ports or the morcellation tool itself. Examples of such tissue morcellation are found in laparoscopic nephrectomies, splenectomies, or laparoscopic supracervical hysterectomies.

In all laparoscopic cases for bulk removal of entire organs, it is advantageous to morcellate the tissue into large tissue segments, rather than small tissue breakups, which then can be removed in very few extraction steps. Apart from time savings, the removal of large tissue segments, rather than small tissue chips, also reduces the chance of cross-contamination with malignant or cancerous tissue. Specifically for the example of laparoscopic supracervical hysterectomies, it is advantageous to morcellate the severed uterus along the surface of the fundus (generating a continuous tissue peel), rather than to repetitively core into the bulk of the uterus (generating a multitude of tissue chips).

To accomplish laparoscopic tissue morcellation and extraction, the tissue is usually first seized with a grasper or tenaculum that is inserted into the abdomen through the inner lumen of the morcellator shaft. In order to maintain pneunoperitoneum, the grasper or tenaculum is sealed against the morcellator shaft by a duck bill valve or floating seal arrangement. After engaging a motor/drive mechanism to cause rotation of the hollow, cylindrical cutting tube, the tissue is continuously cut as it is pulled into the morcellator shaft. As a result, either small tissue fragments or rather large tissue peels can be removed from the abdomen through the morcellation tool.

Ideally, the tissue or organ is simultaneously manipulated with a second set of laparoscopic tools so as to place the tissue in a favorable position in respect to the tissue morcellator. In the case of morcellation and removal of uteri in laparoscopic hysterectomies, for example, it is advantageous to manipulate the severed uterus in a rotating fashion in respect to the morcellator. This allows "peeling" of the fundus in a continuous tissue strip while simultaneously removing it out of the body cavity.

Although morcellators based on cylindrically rotating cutting tubes enable much faster and more practical tissue removal than tissue "chipping" devices, they do show some practical and functional disadvantages.

One drawback is that the tissue cannot be visualized as it is being pulled into the morcellator. When tissue or bits of tissue are pulled through the morcellator during cutting and extraction, small pieces of tissue can be left within the shaft or seal portion of the device. These pieces might be pushed back into the abdomen without being noticed when an instrument is inserted.

Another disadvantage of this arrangement is that both the shaft and the opened jaws of the grasper or tenaculum may damage the edge of the cylindrical cutting blade during manipulation, dramatically reducing its effectiveness and life.

A functional disadvantage of the rotating cylindrical cutting tube design is that tissue can rotate along the longitudinal axis of the cylindrical cutting tube. This is especially the case if the tissue is in contact with the inner lumen of the rotating cutting tube, and is pronounced for rather small-sized and light tissue sections. An arrangement of stationary inner sleeve tubes remedy this problem only partially if the tissue still has contact with a section of the cutting cylinder.

Another practical disadvantage of current cutting tube arrangements in terms of continuous tissue removal is that tissue being fed into the morcellator in a rotating fashion, which allows peeling of the tissue, can overspill beyond the opening of the morcellator. This prevents the remaining bulk tissue from being further rotated into the opening of the morcellator, and interrupts the continuous peel.

SUMMARY

The presented invention provides an apparatus for improved tissue morcellation and extraction used in minimally invasive surgery, particularly laparoscopic surgery.

In one aspect, a tissue morcellation device includes a first, outer cylindrical tube that is transparent, a second, inner cylindrical tube that is transparent and positioned concentrically within a lumen of the first, outer tube, and a tissue guide positioned within the first, outer tube. A distal end of the second, inner tube has a sharpened edge. The second, inner tube is rotatable in relation to the first, outer tube about a longitudinal axis of the second, inner tube. The second, inner tube is also movable longitudinally along the longitudinal axis within the first, outer tube between a first, exposed condition, in which the sharpened distal edge of the second, inner tube is positioned distal a distal end of the first, outer tube, and a second, hidden position, in which the sharpened distal edge of the second, inner tube is positioned proximal the distal end of the first, outer tube and within the lumen of the first, outer tube. The tissue guide is extendable from a first, retracted position in which the tissue guide does not extend distally beyond the distal end of the first, outer tube to a second, extended position in which the tissue guide projects distally of the distal end of the first, outer tube.

The tissue morcellation device may include a third, inner cylindrical tube that is transparent and positioned concentrically within a lumen of the second, inner tube. The third, inner tube is stationary in relation to the first, outer tube. The second, inner tube may have a metallic cutting ring mounted on a distal portion of the second, inner tube. The metallic cutting ring has a sharpened distal edge that forms the sharpened distal edge of the second, inner tube. Alternatively, the distal edge of the second, inner tube is sharpened to provide the sharpened distal edge of the second, inner tube. The tissue morcellation device may include a vibrating element for facilitating the rotational cutting performed by the second, inner tube. The second, inner tube may be adapted to oscillate rotationally about the longitudinal axis in relation to the first, outer tube. If adapted to oscillate, the second, inner tube reversibly rotates between 10° and 30° about the longitudinal axis. When the third, inner cylindrical tube is present, the second, inner tube oscillates between the first, outer tube and the third, inner tube. Alternatively, the second, inner tube and the third, inner tube may be adapted to oscillate in opposite directions. The tissue morcellation device may include a vibrating element for facilitating the oscillation cutting performed by the second, inner tube and the third, inner tube. The sharpened edge at the distal end of each of the second, inner tube and third, inner tube may be serrated. The tissue morcellation device may include a seal for sealing against surgical devices inserted through the tissue morcellation device. The tissue morcellation device may also include a tenaculum having a shaft and a spacer positioned concentrically on the shaft. The outer diameter of the spacer provides a loose fit between the spacer and a lumen wall of the second, inner tube, or the third, inner tube, when provided, to prevent the shaft of the tenaculum from touching the sharpened distal edge of the second, inner tube during manipulation of the tenaculum. The tenaculum may include a handle that is configured to supply a rotating motion along an axis of the connecting shaft. In this manner, tissue that is engaged with the cutting, distal end of the second, inner tube is twisted by the rotary action of the tenaculum so that the diameter of the tissue is reduced for easy withdrawal from within the tissue morcellation device. The tissue morcellation device may include a vibration source adapted to vibrate the second, inner tube. The vibration source is adjusted to facilitate tissue cutting with the second, inner tube with no rotational movement of the second, inner tube. The tissue morcellation device may also include a hand-piece that has a mechanical gear mechanism for generating rotation of the second, inner tube.

Many of the attendant features of the present invention will be more readily appreciated as the same becomes better understood by reference to the following detailed description and considered in connection with the accompanying drawings in which like reference symbols designate like parts throughout.

BRIEF DESCRIPTION OF THE DRAWINGS

The present invention may best be understood by reference to the following description, taken in connection with the accompanying drawings in which the reference numerals designate like parts throughout the figures thereof and wherein.

DETAILED DESCRIPTION

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the structures and/or methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a method and apparatus for the morcellation and extraction of body tissue or organs.

Figure 1:
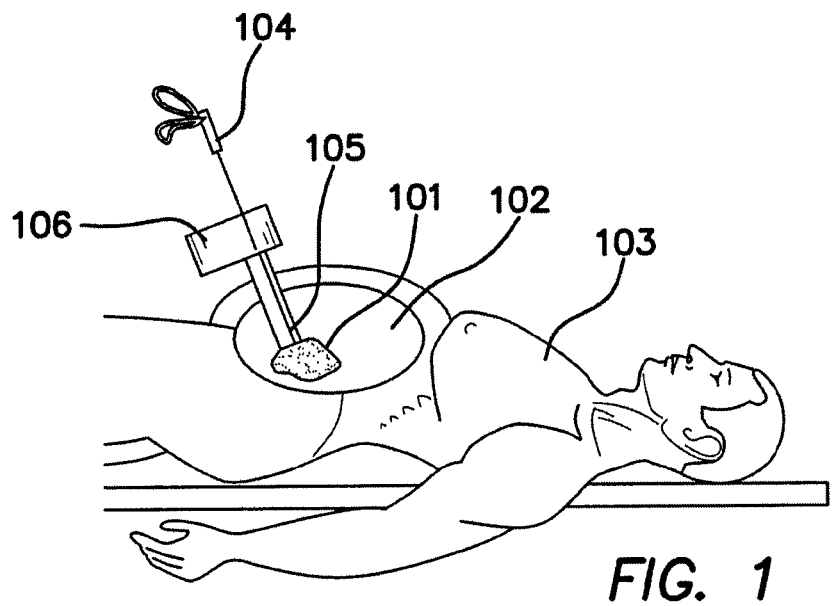
FIG. 1 is a perspective drawing of a tissue morcellator being inserted into the abdominal cavity of a patient for the extraction of body tissue or organs.

Referring now to FIG. 1, the process of removing large-sized body tissue 101 or an organ is demonstrated for a laparoscopic procedure, which requires very small incisions to gain access to the insufflated peritoneal cavity 102 of a patient 103. After the organ or body tissue 101 has been severed from the patient, it can be removed from the abdominal cavity by seizing it with a grasper or tenaculum 104 and pulling it through the inside lumen of a shaft 105 of a hand-held laparoscopic morcellation device 106. The most distal portion of the morcellation device includes a mechanical cutting mechanism that reduces the size of the grasped tissue to fit into the inner lumen of the morcellation device 105. As a result, the two main functions of the morcellation device are to reduce the size of the tissue or organ to be removed and to allow extraction of the morcellated tissue through the inside lumen of the device.

Figure 2:
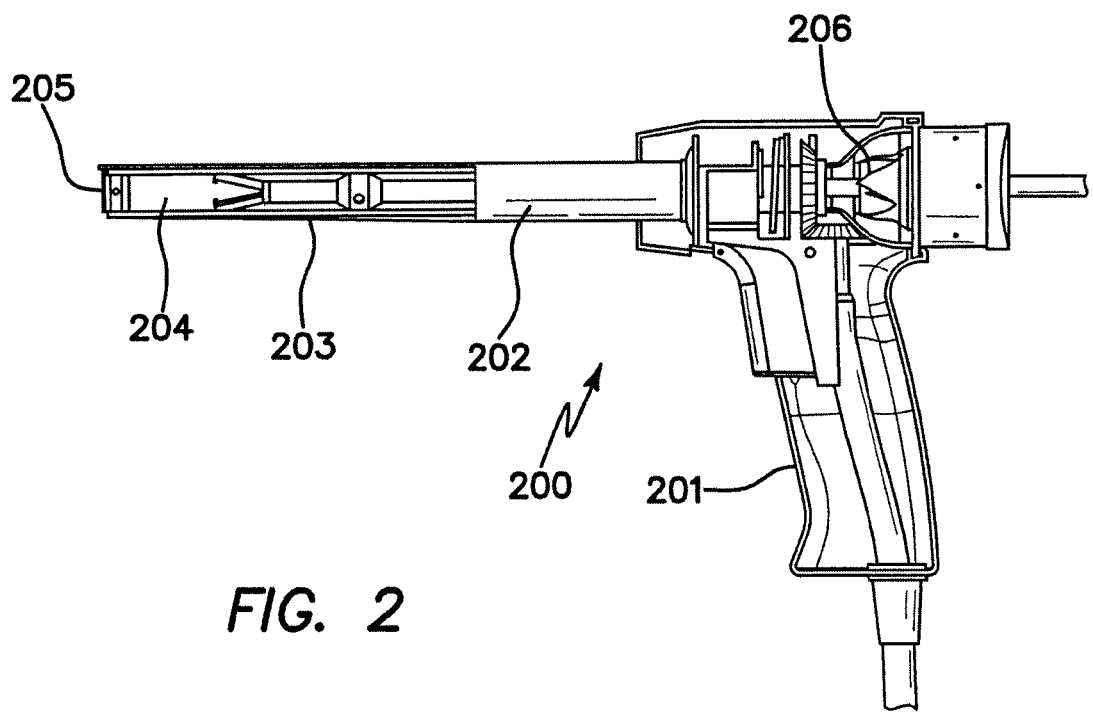
FIG. 2 is a perspective drawing of a visually transparent morcellator.

The working principle of a visually transparent morcellation device 200 is illustrated in FIG. 2, showing the hand-piece 201 and three concentric transparent tubes of the device 202-204. More particularly, the morcellation device has a first, outer tube 202, a second, inner tube 203 positioned within a lumen of the first, outer tube, and a third, inner tube 204, positioned within a lumen of the second, inner tube. While both the outermost 202 and innermost 204 cylindrical tubes are stationary, a mechanical gear mechanism in the handpiece 201 generates rotation of the center hollow cylindrical tube 203. The distal end of this cylindrical tube is provided with a sharpened edge 205 and is used to cut the tissue to be removed. The second, inner tube 203 is capable of rotating in relation to the first, outer tube 202 about a longitudinal axis of the second tube 203. Moreover, the second, inner tube 203 is enclosed in the stationary first, outer tube 202 and can be moved longitudinally in respect to the same along the longitudinal axis so that the sharpened distal end of the second tube is either in an exposed condition, in which the sharpened distal edge of the second tube is positioned distal a distal end of the first, outer tube, and a hidden condition, in which the sharpened distal edge of the second tube is positioned proximal the distal end of the first tube and within the lumen of the first tube. Also shown in FIG. 2 is a seal or septum 206 that enables the surgeon to maintain the peritoneal insufflation during insertion and extraction of the tissue-grasping tenaculum. The seal or septum 206 seals against surgical devices inserted through the tissue morcellation device.

Figure 3A:
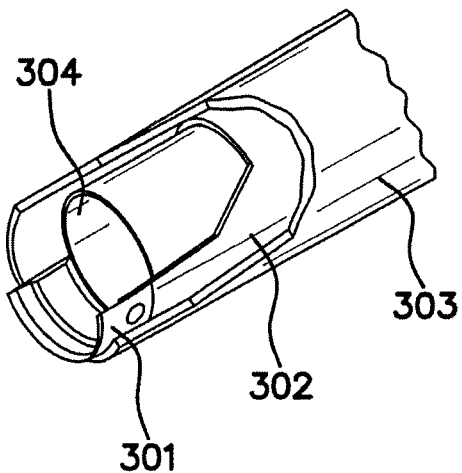
FIGS. 3a through 3c are close-up drawings of the distal part of a visually transparent morcellator shaft.
Figure 3B:
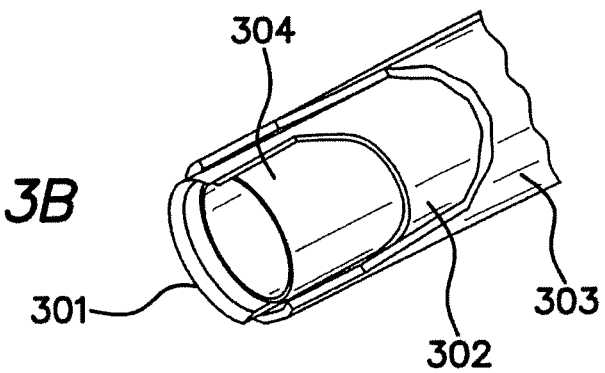
Figure 3C:
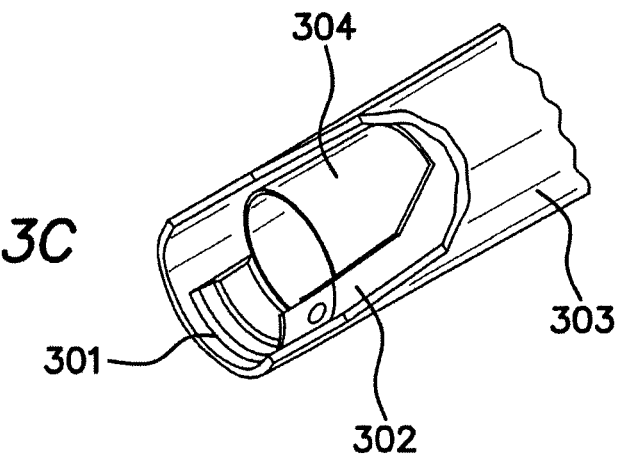

Possible configurations of visually transparent tubular arrangements are shown in FIGS. 3a and 3b for extended, and in FIG. 3c for a retracted blade position. In FIG. 3a, a sharpened metallic cutting ring 301 is mounted on a distal portion of the visually transparent, rotating cutting cylinder 302. The metallic cutting ring 301 has a sharpened distal edge forming the sharpened distal edge of the second, inner ring. Alternately, the edge of the transparent cannula can be sharpened to be used as the blade 301 itself, as shown in FIG. 3b. Also shown in FIGS. 3a, 3b and 3c is the visually transparent outer sleeve 303, as well as inner tube 304 whose entire function is to prevent the tissue from rotating as it is being pulled through the inner lumen of the device. To prevent the plastic or metallic blade from inadvertently touching and damaging tissue, the cutting tube 302 can be retracted within the outer cylindrical tube 303, as shown in FIG. 3c.

Figure 4:
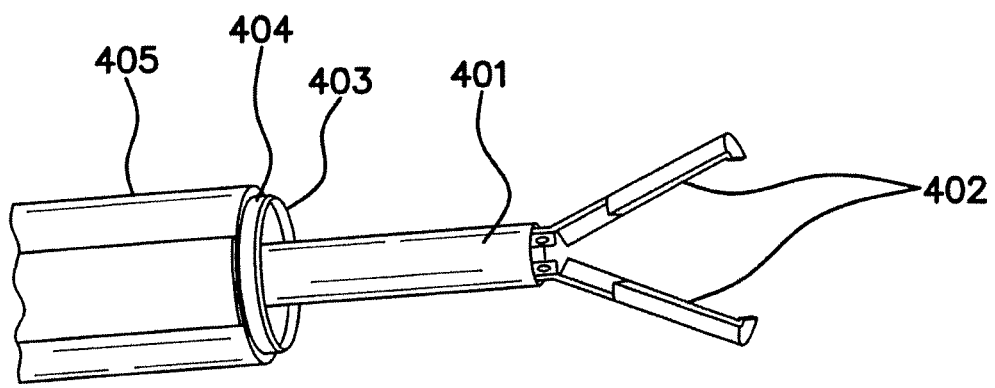
FIG. 4 is a schematic drawing of a grasper or tenaculum being inserted into the morcellator cannula.

The insertion of a laparoscopic grasper or tenaculum 401 through the inside lumen of the tubular morcellation device into the peritoneal cavity is depicted in FIG. 4. After insertion of the closed tool, the tissue is firmly grasped by the jaw elements 402. The tissue can then be pulled against the cutting edge 403 of the circulating cutting tube 404, which has been extended out of the outer sleeve 405 of the tool. As the grasper is being pulled into the tool, continuous cutting of the tissue by the circular blade 403 leads to removal of a tissue strip out of the peritoneal cavity.

Figure 5:
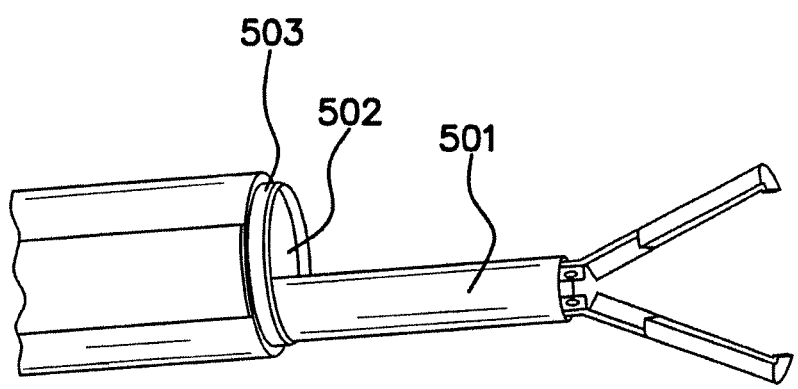
FIG. 5 shows the shaft of the grasper or tenaculum being moved against the cutting blade of the morcellator.

When using a tenaculum or grasper 501 with a shaft diameter significantly smaller than the inner diameter of the inside tube 502, it is unfortunately possible to damage the sharp cutting edge 503 of the morcellation device. This is illustrated in FIG. 5, where manipulation of the shaft of the grasper or tenaculum is damaging the extended and rotating cutting blade. This strongly reduces the effectiveness and life of the morcellation device, making it possibly necessary to use a second device during the same procedure. Alternatively, the cutting blade can also be damaged when the opened jaws are being pulled into the cutting device.

Figure 6:
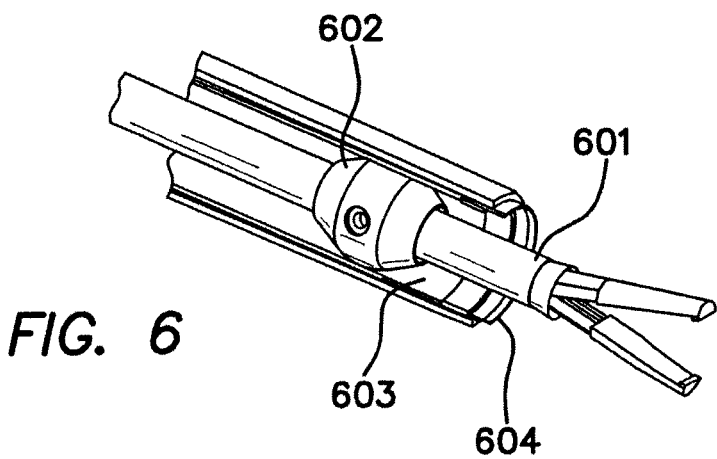
FIG. 6 is a perspective drawing of the grasper or morcellator shaft being applied with a sleeve to prevent damaging of the blade.

One solution for this common problem is illustrated in FIG. 6. Here, the shaft 601 of the grasper or tenaculum is provided with a concentric sleeve or spacer 602. The outer diameter and tolerance of the spacer provides a loose fit of the spacer with the lumen wall of the stationary third, inner tube 603, preventing the shaft 601 from touching the cutting blade 604 during manipulation of the device. The spacer 602 may be sized and configured to prevent contact between the sharpened distal portions of the morcellation device and the tenaculum, but otherwise allow free movement of the tenaculum within the lumen of the morcellation device.

Figure 7:
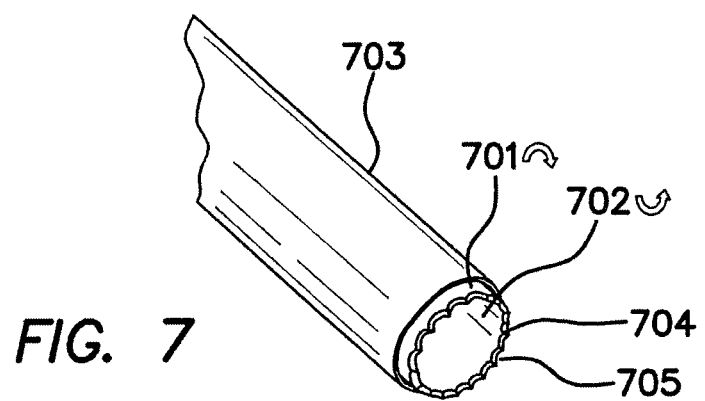
FIG. 7 shows a double-blade arrangement with oscillating cutting tubes.

A different cutting mechanism of the tissue extractor is given in FIG. 7, showing an oscillating tubular structure with at least one tubular structure, such as the second, inner tube 701, being sharpened at the distal end. The first, inner tube may reversibly rotate at least 90 degrees, in relation to the first, outer tube 703, along its longitudinal axis and is driven by a motor and crankshaft. As shown in FIG. 7, two cylindrical cutting tubes, such as the second, inner tube 701 and the third, inner tube 702, are mounted within the stationary first, outer tube 703. Either both tubes 701 and 702 can be oscillating (in opposing direction), or only the outer tube 701 can oscillate while the inner tube 702 remains stationary. When both tubes 701 and 702 oscillate in opposing direction, they may rotate a total of at least 90 degrees in relation to each other; for example, each tube rotating at least 45 degrees in opposite directions. In comparison to the cutting tubes being rotated around the longitudinal axis of the cannulas, the oscillatory movement does not require an inner, stationary tube to prevent rotation of the tissue as it is being pulled through the inner lumen of the morcellation device.

In a preferred embodiment, the speed of the oscillating blade(s) may be varied to accommodate various types of tissue. An extendable-retractable protuberance is associated with a portion of the distal end of the coaxial cover tube of the extractor. The protuberance prevents the cutting element from coring into tissue and facilitates a "peeling" action similar to the peeling of an orange.

An additional embodiment contemplates the use of a vibrating cutting tube where a vibration source is connected to the cutting tube and adjusted to facilitate tissue extraction where no rotational cutting element is used.

A further embodiment combines a vibrating element and an oscillating or rotating cutter so that cutting is facilitated by the vibration of the cutting elements. The vibration may be produced by elements that provide subsonic, sonic or ultrasonic energy distribution.

Also shown in FIG. 7 are the two cutting tubes having serrated cutting blades 704 and 705 at the distal end of the tubes. Again, the cutting blades can either compose of the sharpened cannula edge itself, or of metallic cutting rings being mounted on the distal end of the transparent plastic cannulas.

Figure 8A:
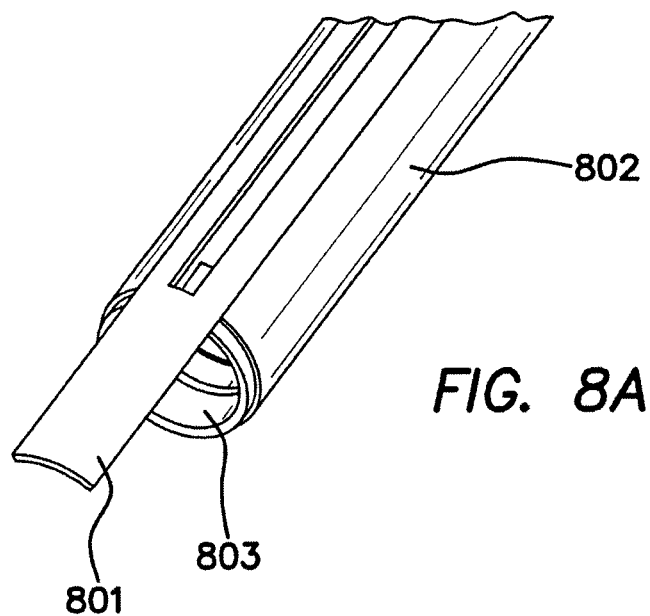
FIGS. 8a and 8b depict a tissue guide or manipulator that has been extended beyond the distal position of the cutting blade (8a), and that has been retracted into the morcellator shaft (8b).
Figure 8B:
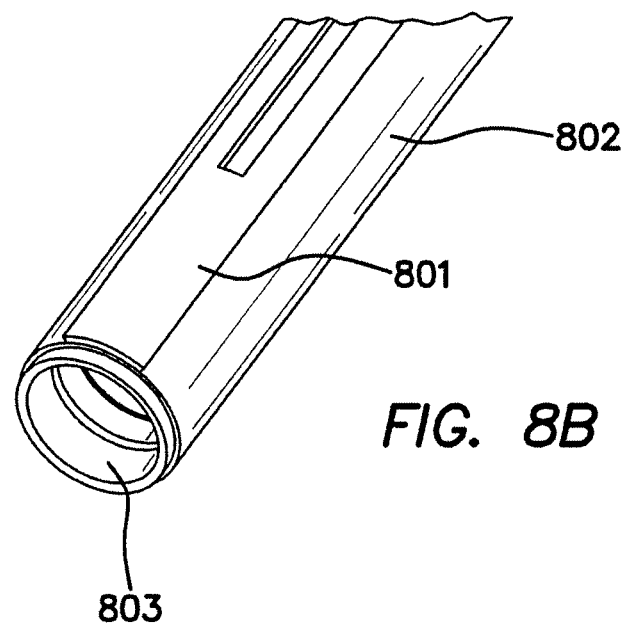

Another arrangement for an improved morcellation and extraction device is given by incorporation of a tissue guide or manipulator 801 positioned within the first, outer tube of the device 802. This is shown in FIG. 8*a* where the tissue guide 801 is in a second, fully extended condition, in which the tissue guide projects distally of the distal end of the first, outer tube, and where the cutting tube 803 has been advanced to the cutting position. The tissue guide can be retracted to a first, retracted position into the first, outer tube material 802, as shown in FIG. 8*b*, in which the tissue guide does not extend distally beyond the distal end of the first, outer tube. Here, in addition to the retraction of the tissue manipulator 801, also the cutting tube 803 has been retracted into the outer tube of the device to disable cutting of tissue.

Figure 9:
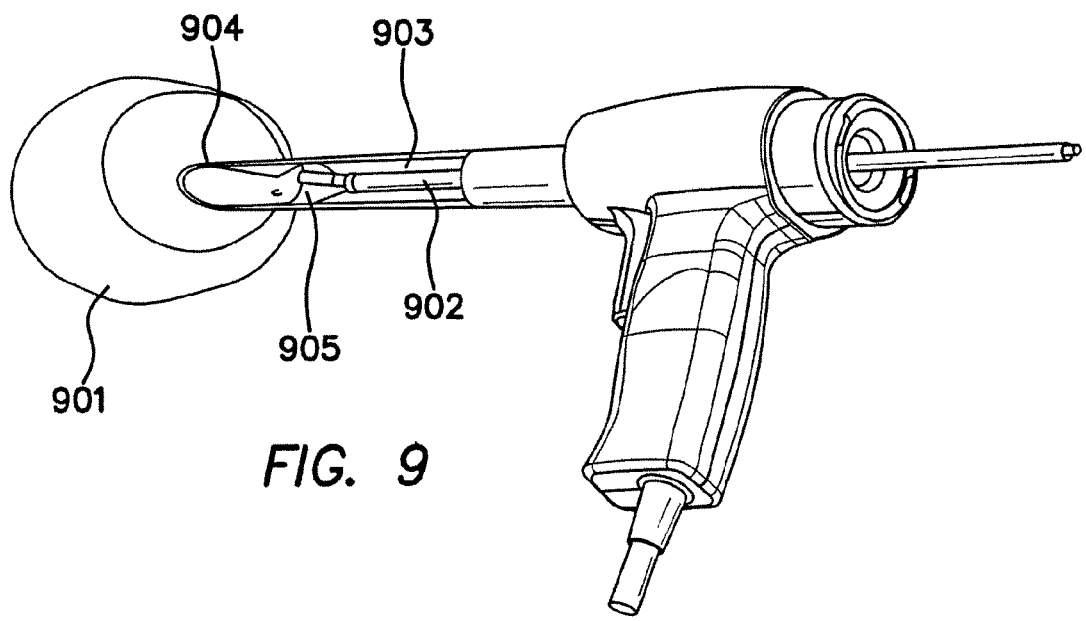
FIG. 9 schematically depicts the working principle of the morcellator with retracted tissue manipulator, allowing the morcellator to core into the bulk of body tissue or an organ.
Figure 10:
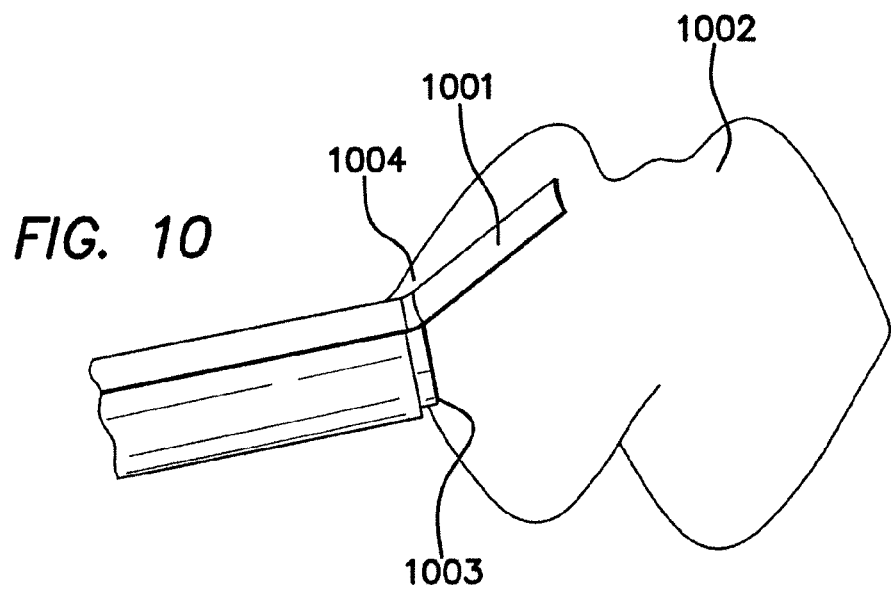
FIG. 10 schematically depicts the working principle of the tissue manipulator preventing the tissue from turning over the morcellator tube as it is guided along the surface of large body tissue or an organ.
Figure 11:
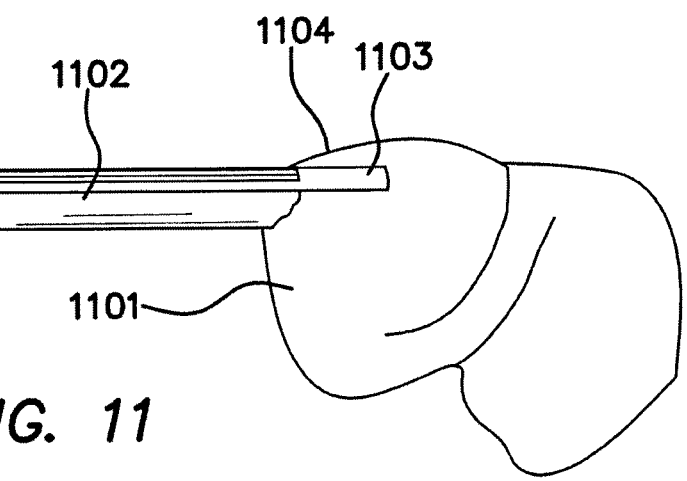
FIG. 11 schematically depicts the working principle of the tissue manipulator preventing the tissue from spinning along the longitudinal axis of the morcellator shaft when the morcellator is not equipped with an inner, stationary shaft.

The working principle of the morcellator device with retracted and extended tissue guide is illustrated in FIG. 9 through FIG. 11, showing the morcellation of large body tissue, such as an organ, as well as the simultaneous removal of the same through the inner lumen of the morcellation device. Referring to FIG. 9, the tissue 901 has been firmly grasped with a laparoscopic grasper or tenaculum 902 that is fed into the peritoneal cavity through the inner lumen 903 of the morcellation device. With rotating or oscillating the extended cutting blade(s) 904, the grasped tissue 905 is pulled into the device where it is cut at the distal edge of the tubular blade. As a result, the cut tissue is slowly moved into the inner lumen of the morcellation device.

Further progress of the tissue morcellation and extraction process strongly depends on how the tissue is delivered in respect to the distal circular opening of the device. As shown in FIG. 9 for a device with a retracted tissue manipulator, the tissue is cut by coring the cutting device into the tissue. Eventually the cutting blade will reach the opposing side of the body tissue or organ, leading to the removal of cylindrical tissue fragment through the device. Subsequent "coring" of the body tissue or organ in the described fashion can be used to remove the entire bulk of the tissue.

A different result is obtained when the tissue is fed into the morcellation device with an extended tissue manipulator 1001, as shown in FIG. 10. Here, the tissue guide 1001 will prevent the coring of the bulk tissue and much rather promote morcellation along the surface of the tissue. This in turn allows "peeling" the tissue into long strips, allowing the surgeon to remove large tissue volumes in few extraction steps. The peeling becomes possible as the bulk tissue 1002 starts to rotate towards the tissue manipulator as it is being pulled into the device. At the same time, the tissue manipulator prevents tissue from folding over the opening of the tool 1003, which would cause coring of the device into the tissue. This can even be the case for large tissue enlargements 1004 being pulled into the device.

An additional effect of the tissue manipulator on the morcellation process of a smaller tissue volume 1101 is illustrated in FIG. 11. In absence of an inner stationary tube, or if a recessed inner stationary tube exposes a significant amount of the cutting tube, friction of the tissue with the inner lumen of the cutting tube, or with the exposed section of the cutting tube, can cause the bulk tissue to spin around the longitudinal axis of the tube 1102. This is prevented by the extension of the tissue guide 1103 since tissue section 1104 will be pushed against one side of the guide 1103, which prevents tissue 1101 from rotating.

Figure 12:
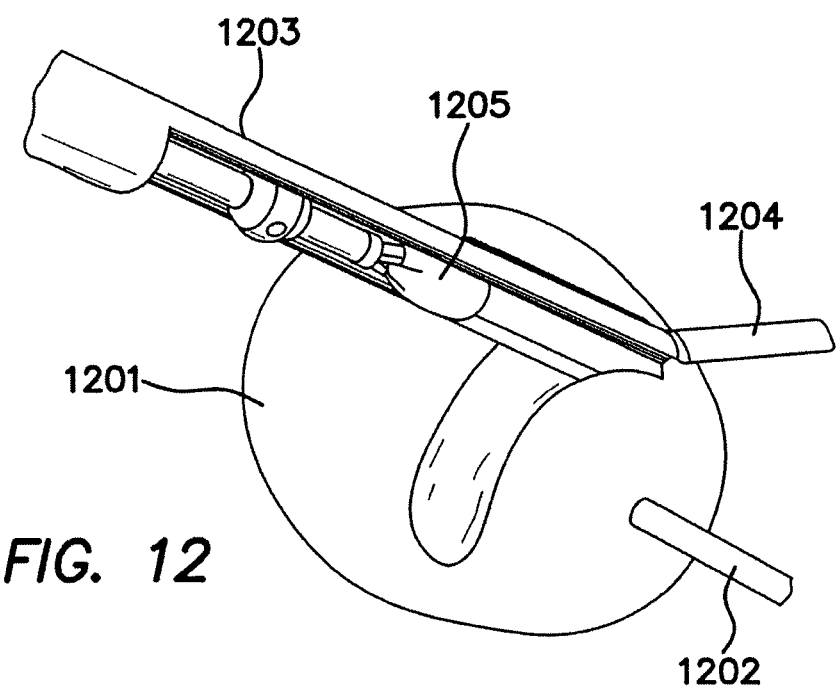
FIG. 12 is a perspective drawing of a laparoscopic device that is used to rotate body tissue or an organ in order to facilitate the tissue morcellation process.

Still another aspect of the present invention is depicted in FIG. 12. Here, the bulk tissue or organ 1201 has first been cored in the fashion described above, and is then secured with a "tissue-delivering" device 1202. The device is manipulated by a co-surgeon and slowly rotates the bulk tissue or organ around the longitudinal axis of the device 1202. A morcellation device 1203 with extended tissue guide 1204 is positioned along the surface of the bulk tissue as shown. When grasping tissue with a grasper or tenaculum and pulling the tissue into the activated device, the rotation of the bulk tissue allows the surgeon to continuously feed the cut tissue 1205 into the morcellation device from where it can be extracted out of the abdominal cavity.

Figure 13:
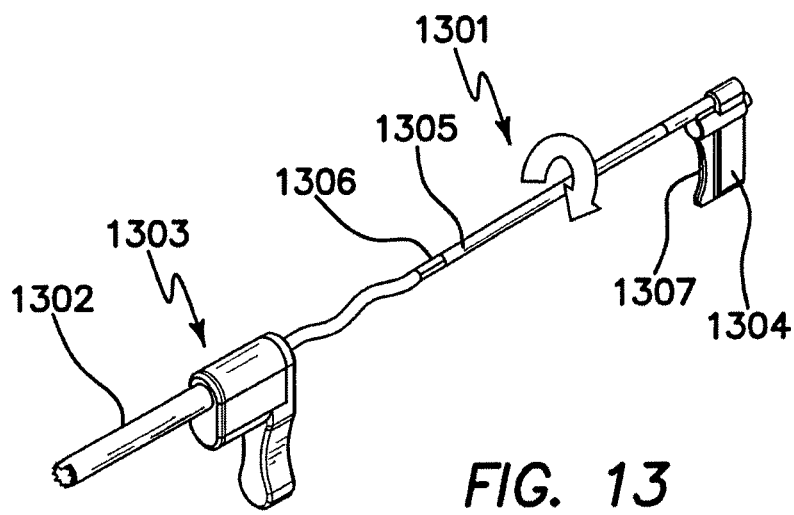
FIG. 13 is a perspective drawing of a laparoscopic device that is used to rotate body tissue or an organ in order to facilitate the tissue morcellation process.

Yet another aspect of the present invention is given in FIG. 13, showing a tenaculum or grasper 1301 that is sized and configured to work through the open channel of a tubular structure 1302 associated with a tissue extractor 1303 comprising a handle 1304, connecting shaft 1305 and a pair of opposing grasping jaws 1306. The handle is configured to supply a rotating motion along the axis of the connecting shaft. Tissue that is engaged to the cutting end of the extractor tube is further twisted by the rotary action of the tenaculum so that the diameter of the tissue is reduced for easy withdrawal from within the extractor tube. The rotary action may be supplied by a helical drive associated with a lever 1307 attached to the handle 1304 or may be supplied by an electric motor. The twisted tissue within the cutting tube of the extractor resembles rope and is reduced in diameter as it is elongated and twisted simultaneously.

Figure 14:
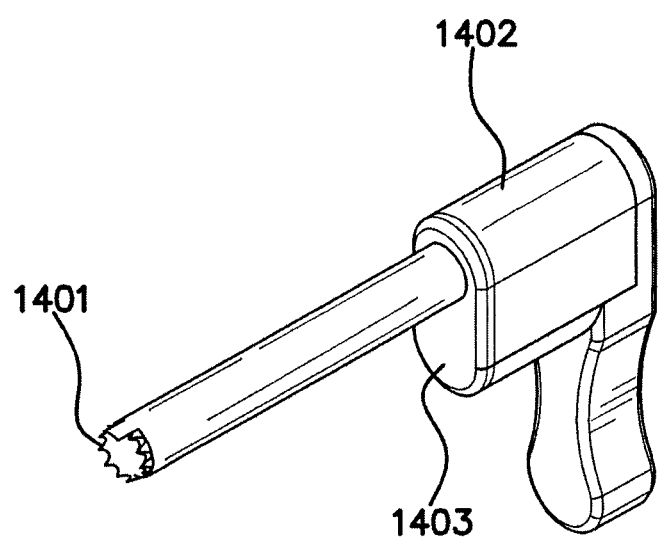
FIG. 14 is a perspective drawing of an alternate preferred embodiment of a self-powered, laparoscopic device that is used to extract or morcellate body tissue or organs.

FIG. 14 illustrates an embodiment of the present invention where the cutting element 1401 is powered by a motor within the handle 1402 of the device. The power source for the motor may be external or it may be an internal battery or battery pack 1403.

Many alterations and modifications may be made by those having ordinary skill in the art without departing from the spirit and scope of the invention. For these reasons, the above description should not be construed as limiting the invention, but should be interpreted as merely exemplary of the embodiments. Accordingly, it is not intended that the invention be limited, except as by the appended claims.

We claim:

1. A tissue morcellation device, comprising:
a handpiece;
a first outer cylindrical tube defining a first lumen; the first outer tube being connected to the handpiece;
a second inner cylindrical tube defining a second lumen; the second inner tube being positioned concentrically within the first lumen of the first outer tube;
the second inner tube having a sharpened distal end adjacent to a distal end of the first outer tube; the second inner tube being configured to rotate relative to the first outer tube about a longitudinal axis of the second inner tube to effect morcellation of tissue at the sharpened distal end so as to reduce the size of the tissue to be extracted; rotary motion being supplied to the second inner tube by an electric motor; and
a third inner cylindrical tube, the third inner tube being positioned concentrically within the second lumen of the second inner tube; the third inner tube being stationary relative to the first outer tube;
wherein the second inner tube is movable relative to the first outer tube along the longitudinal axis between a first exposed condition in which the sharpened distal end of the second inner tube is positioned distally of the distal end of the first outer tube, and a second hidden position in which the sharpened distal end of the second inner tube is positioned proximally of the distal end of the first outer tube and within the first lumen;
a tenaculum having a shaft and a spacer; the shaft having an outer surface and the spacer being positioned concentrically on the outer surface of the shaft, the spacer being fixedly attached to the outer surface of the shaft of the tenaculum, wherein, an outer diameter of the spacer provides a loose fit between the spacer and a lumen wall of the third inner tube to prevent the shaft of the tenaculum from touching the sharpened distal end during manipulation of the tenaculum.

2. The tissue morcellation device of claim 1, the tenaculum further comprising:

a handle configured to supply a rotating motion along an axis of the tenaculum shaft, such that tissue that is configured to engage with the sharpened distal end of the second inner tube is twisted by a rotary action of the tenaculum so that a diameter of the tissue is reduced for withdrawal from within the tissue morcellation device.

3. The tissue morcellation device of claim 2 wherein the rotary action of the tenaculum is supplied by an electric motor.

4. A tissue morcellation device, comprising:

a handpiece;

a first outer cylindrical tube defining a first lumen; the first outer tube being connected to the handpiece;

a second inner cylindrical tube defining a second lumen; the second inner tube being positioned concentrically within the first lumen of the first outer tube; the second inner tube having a sharpened distal end adjacent to a distal end of the first outer tube; the second inner tube being configured to rotate relative to the first outer tube about a longitudinal axis of the second inner tube to effect morcellation of tissue at the sharpened distal end so as to reduce the size of the tissue to be extracted;

a third inner cylindrical tube, the third inner tube being positioned concentrically within the second lumen of the second inner tube; the third inner tube being stationary relative to the first outer tube; and a grasper longitudinally movable within the third inner cylindrical tube and configured to grab tissue at the distal end; the grasper including an elongate shaft having a shaft diameter and a shaft outer surface and a spacer positioned concentrically on the shaft outer surface; the spacer being fixedly attached to the shaft outer surface and extending radially outwardly from the shaft outer surface to form a spacer diameter that is larger than the shaft diameter; wherein the spacer diameter is smaller than an inner diameter of the third inner tube to provide a loose fit between the spacer and inner wall of the third inner tube.

5. The tissue morcellation device of claim 4 wherein the grasper is configured to be rotatable.

6. The tissue morcellation device of claim 5 wherein rotary motion of the shaft of the grasper is supplied by an electric motor.

7. The tissue morcellation device of claim 5 wherein rotary motion is supplied by a helical drive associated with a lever attached to a handle of the grasper.

8. The tissue morcellation device of claim 4 wherein the grasper further comprises a handle at a proximal end of the grasper configured to supply a rotating motion about a longitudinal axis of the elongate shaft of the grasper.

9. The tissue morcellation device of claim 4 wherein the grasper is configured to be rotatable with respect to the first outer tube such that tissue that is configured to engage with the sharpened distal end of the second inner tube is twisted by a rotary action of the grasper so that the tissue is reduced for withdrawal from within the tissue morcellation device.

10. The tissue morcellation device of claim 9 wherein the rotary action of the grasper is supplied by an electric motor.

11. A tissue morcellation device, comprising;

a handpiece;

a first outer cylindrical tube defining a first lumen; the first outer tube being connected to the handpiece;

a second inner cylindrical tube defining a second lumen; the second inner tube being positioned concentrically within the first lumen of the first outer tube; a distal end of the second inner tube having a sharpened distal end adjacent to a distal end of the first outer tube; the second inner tube being configured to rotate relative to the first outer tube about a longitudinal axis of the second inner tube to effect morcellation of Page 6 of 16 rotary motion being supplied to the second inner tube by an electric motor; and a third inner cylindrical tube, the third inner tube being positioned concentrically within the second lumen of the second inner tube; the third inner tube being stationary relative to the first outer tube; and a grasper longitudinally movable within the third inner cylindrical tube and configured to grab tissue at the distal end; the grasper including a handle and an elongate shaft having an axis, a shaft diameter and a shaft outer surface and a spacer positioned concentrically on the shaft outer surface; the spacer being fixedly attached to the shaft outer surface and extending radially outwardly from the shaft outer surface to form a spacer diameter that is larger than the shaft diameter; wherein the handle of the grasper is configured to supply a rotating motion along the axis of the elongate shaft;

wherein the spacer diameter provides a loose fit between the spacer and inner wall of the third inner tube to prevent the elongate shaft of the grasper from touching the sharpened distal end of the second inner tube during manipulation of the grasper.

12. The tissue morcellation device of claim 11 wherein rotary motion of the elongate shaft is supplied by an electric motor.

13. The tissue morcellation device of claim 11 wherein the diameter of the spacer increases from distal and proximal ends of the spacer.

14. The tissue morcellation device of claim 11 wherein the spacer extends radially outwardly from the shaft at an angle.

15. The tissue morcellation device of claim 11 wherein the spacer is spherical in shape.

* * * * *